United States Patent [19]
Bleicher

[11] Patent Number: 5,922,890
[45] Date of Patent: Jul. 13, 1999

[54] ORGANIC COMPOUNDS

[75] Inventor: Konrad Bleicher, Freiburg i.Br., Germany

[73] Assignee: Novartis AG, Basel, Switzerland

[21] Appl. No.: 08/984,639

[22] Filed: Dec. 3, 1997

[30] Foreign Application Priority Data

Dec. 4, 1996 [GB] United Kingdom .................. 9625167

[51] Int. Cl.$^6$ .......................... C07C 63/06; C07C 233/65
[52] U.S. Cl. .......................... 552/106; 552/104; 552/105; 552/111; 552/113; 552/115; 536/27.14
[58] Field of Search .................. 552/104, 105, 552/106, 111, 113, 115; 536/27.14

[56] References Cited

U.S. PATENT DOCUMENTS

| | | | |
|---|---|---|---|
| 3,440,190 | 4/1969 | Melby | 260/17.4 |
| 5,612,474 | 3/1997 | Patel | 536/27.14 |

FOREIGN PATENT DOCUMENTS

| | | |
|---|---|---|
| 0 424 819 A1 | 5/1991 | European Pat. Off. . |
| 43 06 839 A1 | 9/1994 | Germany . |

OTHER PUBLICATIONS

Bayer et al., Peptides (1994), Proceedings of the 23 EPS, Sep. 4–10, 1994 Braga, Portugal, pp. 201–202.
Derwent Abstracts, 85–304864/49 (EP–163406–A) (1985).
Chemical Abstracts, 95:80696 (1981).
Chemical Abstracts, 114–122939 (1991).
Chemical Abstracts, 125:131829 (1996).
Chemical Abstracts, 120–324197 (1994).
Chemical Abstracts, 125:87208 (1996).
Chemical Abstracts 76:107840 (1972).
Chemical Abstracts 112–55123 (1990).
Chemical Abstracts 78:136730 (1973).
Chemical Abstracts, 125:143287 (1996).
Chemical Abstracts, 122:56551 (1995).
Derwent Abstracts, 94–349957 [44], (DE 453 06 839 Al) (1994).
Chemical Abstracts, 104:91186 (1986).
Chemical Abstracts Registry No. 78500–58–0 (1996).
Chemical Abstracts Registry No. 100698–65–5 (1996).
Chemical Abstracts Registry No. 279615–27–1 (1996).
Chemical Abstracts Registry No. 172976–68–0 (1996).
Chemical Abstracts Registry No. 155180–29–3 (1996).
Chemical Abstracts Registry No. 155180–30–6 (1996).
Chemical Abstracts Registry No. 132454–39–8 (1996).
Chemical Abstracts Registry No. 35960–00–0 (1996).

*Primary Examiner*—Richard L. Raymond
*Attorney, Agent, or Firm*—Gregory D. Ferraro

[57] ABSTRACT

New trityl linkers for use in solid phase synthesis comprise compounds of formula II

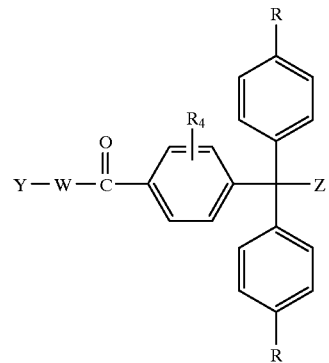

wherein
$R_4$ is alkyl (e.g. $C_{1-4}$ alkyl), halogen, $NO_2$, or hydrogen;
Z is a coupling group chosen from acylamido, acyloxy, amino, halogen, thiol or hydroxyl,
where acyl is the residue of a carboxylic acid or a residue of formula $R_5CO$ where $R_5$ is an organic group;
Y is H, a reactive functional group or an attachment to a solid phase;
W is O when Y is H or a reactive functional group, or W is —NH—, or —$NR_6$—(urethane) when Y is an attachment to a solid phase,
where $R_6$ is an organic group and,
each R which, may be the same or different, is $C(O)NR_7R_8$, $CF_3$, F or Cl wherein each $R_7$ and $R_8$, which may be the same or different, is H or $C_{1-4}$ lower alkyl
which are suitable for use as linkers in solid phase syntheses in which moderate to strongly acidic conditions are used during synthesis steps or in which strongly acidic conditions are required to recover product from the solid phase.

7 Claims, No Drawings

ORGANIC COMPOUNDS

This invention relates to trityl compounds and in particular to the use of trityl compounds as linkers for solid phase chemical synthesis.

Published German patent application DE 43 06 839 A1 describes a solid phase system containing a trityl group bonded via a second order substituent to a solid phase carrier, in which said solid phase system is of formula I

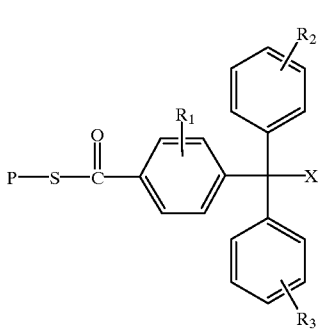

wherein

P is a solid phase carrier material;

S is a spacer group chosen from alkyl, —NH—, —NR— (urethane), or —O— (ester);

one or more of $R_1$, $R_2$ and $R_3$ are substituents, which may be the same or different, chosen from alkyl, alkoxy, dialkylamino, halogen, $NO_2$, or hydrogen, and X is a coupling group chosen from acylamido, acyloxy, amino, halogen, hydroxyl or phosphonate, where acyl is the residue of a carboxylic acid or a residue of formula RCO where R is an organic group, and the use of this system as a linker in the solid phase synthesis of, e.g. peptides, glycopeptides, nucleotides and proteins. It is stated that this system has the advantage that only mild conditions, e.g. acetic acid in dichloromethane/methanol, are required to remove synthesised products from the carrier such that protecting groups are retained and unwanted side reactions are suppressed. The only compounds for which the synthesis is specifically described in DE 43 06 839 A1 are p-carboxytritylalcohol derivatives in which $R_1$, $R_2$ and $R_3$ are all hydrogen.

The p-carboxytritylalcohol based linker specifically described in DE 43 06 839 A1 is not suitable for use in syntheses in which acidic conditions, in particular moderate to strong acidic conditions, e.g. from 2 to 10% trifluoroacetic acid in dichloromethane and other similar acids, are used during synthesis steps, or strongly acidic conditions are required to recover product from the solid phase. We have now devised new trityl-based linkers for use in solid phase syntheses in which moderate to strongly acidic conditions are used during synthesis steps or in which strongly acidic conditions are required to recover product from the solid phase.

Accordingly the present invention provides a compound of formula II

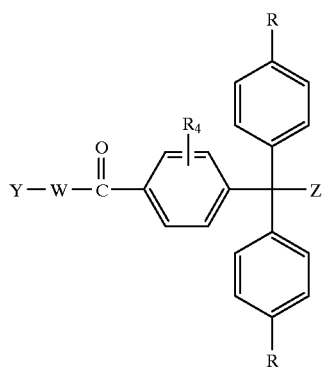

wherein $R_4$ is alkyl (e.g. $C_{1-4}$alkyl), halogen, $NO_2$, or hydrogen;

Z is a coupling group chosen from acylamido, acyloxy, amino, halogen, thiol or hydroxyl, where acyl is the residue of a carboxylic acid or a residue of formula $R_5CO$ where $R_5$ is an organic group;

Y is H, a reactive functional group or an attachment to a solid phase;

W is O when Y is H or a reactive functional group, or W is —NH—, or —$NR_6$— (urethane) when Y is an attachment to a solid phase, where $R_6$ is an organic group and, each R which, may be the same or different, is $C(O)NR_7R_8$, $CF_3$, F or Cl wherein each $R_7$ and $R_8$, which may be the same or different, is H or $C_{1-4}$ lower alkyl.

Preferably $R_4$ is hydrogen.

Preferably Z is OH or halogen, most preferably halogen, especially chlorine.

Preferably W is —O— or —NH—.

Preferably each R is the same. Preferably each R is F or Cl, especially Cl.

In a particular embodiment the invention provides a solid phase synthesis system of formula II, wherein $R_4$, Z, W and R are as defined above and Y represents an attachment to a solid phase support material. Suitable solid phase support materials are described in DE 43 06 839 A1, including naturally occurring or synthetic organic or inorganic polymers in particulate form, e.g. as beads, or preferably as a surface coating or layer on a suitable inert substrate material. Examples of suitable polymer materials include crosslinked polystyrene or a graft copolymer of polyethylene glycol on polystyrene, e.g. polystyrene pins, Gly-HMD-MA/DMA pins and HEMA pins. Conveniently the polymer comprises surface amino groups, e.g. amino methyl groups, to facilitate attachment of the compound of formula II, e.g. via an —NH— spacer group W.

The solid phase synthesis system may be prepared by coupling a precursor of a compound of formula II, e.g. comprising a reactive functional group with a suitably derivatised or functionalised solid phase material. Conveniently the solid phase material may comprise amino groups to provide an —NH— spacer group W in the compound of formula II. Such processes for the preparation of the solid phase synthesis system are included within the invention.

In accordance with the present invention we have found that the compounds of the invention are particularly suitable as linkers for solid phase synthesis being advantageously resistant to cleavage of product from the solid phase e.g. under mild or moderately acidic conditions. Thus conveniently the compounds of the invention are suitable for use as linkers for solid phase synthesis procedures which employ acidic conditions during synthesis steps and/or require strongly acidic conditions for cleavage of product from the solid phase.

Thus in a further aspect the invention includes use of a compound of formula II as defined above, in particular a solid phase synthesis system of formula II, for solid phase chemical synthesis.

In a yet further embodiment the invention also provides a process for solid phase synthesis, e. g. of an oligomeric product, in which a compound of formula II as defined above is used as a linker and in which the product is cleaved from the solid phase under strongly acidic conditions.

Such solid phase synthesis includes synthesis of peptides, glycopeptides, nucleotides and proteins. Advantageously, however, the compounds of the invention may be used for solid phase syntheses in which acidic conditions, e.g. corresponding to from about 1% up to about 10% or more, more usually from about 1% to about 5%, trifluoroacetic acid (TFA) in 10% methanol (MeOH)/dichloromethane (DCM) or similarly acidic conditions, are employed during one or more synthesis steps. Advantageously also, the compounds of the invention may be used for solid phase syntheses in which strongly acidic conditions, e.g. corresponding to at least 5% TFA/ 10% MeOH/DCM, preferably at least 20% TFA/ 10% MeOH/DCM or especially at least 50% TFA/ DCM (e.g. 95% TFA/5% $H_2O$) or similar acidic conditions are required and/or tolerated for cleavage of the product from the solid phase.

The invention is further described by way of illustration only in the following non-limiting examples.

EXAMPLES

Example 1

Preparation of 4-[bis-(4-Chloro-Phenyl)-Hdroxy-Methyl]-Benzoic Acid

The title compound is prepared as follows from readily available starting materials.

A. Preparation of 4-[bis-(4-Chloro-Phenyl)-Hydroxy-Methyl]-Toluene 63.2 g of magnesium shavings degreased, dried under vacuum and activated with iodine (0.6 g) are placed in a preheated (ca 60° C.) 20 l reaction vessel under an atmosphere of nitrogen. A solution of 342 g of 4-bromotoluene in 3.4 l of tetrahydrofuran (THF) is added, the first 350 ml of the solution being added swiftly followed by slow stirring for some minutes at 65–67° C. until reaction commences as judged by the onset of cloudiness and a lightening of the colour of the reaction mixture beneath the stirrer. The remainder of the solution is then added relatively swiftly over a 30 min period at 65–67° C. after which the dark coloured Grignard solution is stirred for a further 30 min at 65–67° C. and then cooled to 20–25° C.

A solution of 401.6 g of dichlorobenzophenone in 4 l of THF is then added to the Grignard solution over a period of 30 min at 20–25° C. followed by stirring at the same temperature for about 60 min to complete the reaction. The reaction mixture is then cooled to 5–10° C. and 2.75 l of 10% aqueous ammonium chloride solution is added dropwise over a 30 min period. The hydrolised mixture is then stirred at 20–25° C. for a further 30 min after which it is filtered. The aqueous phase is separated and extracted with 2×3 l ethylacetate. The resultant organic phase is then washed with 3 l of 10% ammoniuim chloride solution followed by 3 l of aqueous brine solution. The cleaned organic phase is then dried with magnesium sulphate and filtered and the solvent evaporated in a rotary evaporator at 45–50° C. under reduced pressure (250-20 mbar) to give 660 g of crude 4-[bis-(4-chloro-phenyl)-hydroxy-methyl]-toluene product as a yellowy oil.

B. Preparation of 4-[bis-(4-Chloro-Phenyl)-Hydroxy-Methyl]-Benzoic Acid 1184 g of the crude 4-[bis-(4-chloro-phenyl)-hydroxy-methyl]-toluene product obtained above is dissolved in 17.5 l of tertiary butanol and 26.5 of water is added rapidly at 20–25° C. to give a cloudy solution. 475 g of Sodium carbonate is then added and the mixture warmed to 70–72° C. The solution is divided into equal portions and a total of 1900 g of potassium permanganate is added at 70–72° C. within a 6 h period under a constantly flowing (ca 1–2 l/min) stream of argon, after which the mixture is stirred over night (ca 16 h) at 70–72° C. under the argon stream, and then cooled to 20–25° C. 1.2 l of 10% sodium bisulphite is then added, the mixture stirred for 30 min at 20–25° C. and the presence of excess oxidising agent checked with acidified cadmium iodide starch paper. After a further ca 0.6 l of sodium bisulphite solution is added the blue colouration is no longer obtained with the test paper. When the peroxide test is negative, the reaction mixture is warmed to 40–45° C. and 660 ml of concentrated sulphuric acid is added dropwise at this temperature to give a final pH of 1–2. The mixture is then stirred for 15 min at 55–60° C., cooled to 30° C. and vacuum filtered.

The completely clear, peroxide-free, pale yellow filtrate is then concentrated by vacuum evaporation of solvent at 60–65° C. and 100-80 mbar. 30 l of ethylacetate is then added to the concentrate and the resultant mixture extracted with a further 40 l of ethylacetate. The aqueous fraction is separated and further extracted. The ethylacetate fraction is washed with 2×20 l of water followed by 20 l of brine solution. The cleaned ethylacetate fraction is dried with magnesium sulphate, filtered, concentrated to ca 20 l by evaporation of solvent under vacuum (ca 250 mbar) at 55–60° C. and then fully concentrated in a rotary evaporator under vacuum (200-20 mbar) at 50° C. The solid crude product is dissolved in 2.1 l of diethylether at 30–35° C., the solution filtered and the clear filtrate mixed with 4.2 l of hexane with slow stirring.

The resultant mixture is allowed to crystallise over night at 20–25° C. with stirring. The white, relatively watery, crystal suspension is cooled to 0–5° C., stirred for 60 min, filtered, washed with ice-cold diethylether/hexane 1:2 and dried at 50° C. under vacuum to give 633 g of a crude, white, crystalline product judged to be about 93% pure by HPLC analysis. This crude crystal product is digested with 1.2 l of diethylether at 30–35° C., the mixture left over night in a cool room at 5° C., vacuum filtered, washed with 300 ml of ice-cold diethylether and dried to give 484 g of purified crystal product, melting point 117–120° C., judged to be about 97% pure by HPLC analysis.

The mother liquor from both the first and second crystallisations is concentrated to give 415 g of a yellowy oil which is mixed with 5 l of isopropylacetate-water mixture and chromatographed (silicagel 63–200 $\mu$m/isopropylacetate-water column, eluent ca 4 l isoprpylacetate-water). The product containing fractions (fractions 3 to 8) are concentrated on a rotary evaporator at 50° C. under vacuum to give about 200 g of crude solid product. This crude product is mixed with 500 ml of diethylether and 400 ml of ethylacetate at 30–35° C. to give a clear solution, which is then mixed with 1l of hexane at 20–25° C. and left to allow the product to crystallise out. The purified crystalline product is recovered by vacuum filtration, washed with ice-cold diethylether and dried to yield 120 g of white crystalline product (melting point 121–123° C.), judged to about 99.5% pure by HPLC analysis.

Particulars of the NMR, IR and MS spectra of the purified title compound are given as follows:

El-MS (l=5.5 v; PT=98° C.):372 (M+, 2%), 355 ([M—OH]+, 4%), 261 ([M—Cl—Ph]+, 34%), 251 ([M—PhCO$_2$H]+, 53%),149 ([HO$_2$C—Phe—CHO]+, 56%), 139 ([ClPhCOH]+, 100%).

IR(KBr): 2978, 1680(CO), 1490, 1401, 1246 (C—OH), 1094 (Cl—Ph), 1013, 858, 836, 825, 811, 792, 772, 539 cm$^{-1}$.

NMR (30 Mhz, CDCl3), aromatic protons: 8.05 (2H,d), 7,4 (2H, d), 7.3 (2H,d), 7.2 (4H,d).

Similarly the compounds 4-[bis-(4-fluoro-phenyl)-hydroxy-methyl]-benzoic acid, 4-[bis-(4-trifluoromethyl-phenyl)-hydroxy-methyl]-benzoic acid and 4-[bis-(4-dimetylcarbamoylphenyl)-hydroxy-methyl]-benzoic acid are analogously prepared.

Example 2

Attachment of the dichlorotrityl linker to the Solid Phase

A solution of 4-[bis-(4-chloro-phenyl)-hydroxy-methyl]-benzoic acid (0.1 M), TBTU (2-(1 H-benzotriazole-1-yl)-1,1,3,3-tetramethyluronium tetrafluoroborate, 0.1 M) and NMM (N-methylmorpholine, 0.2M) in DMF (dimethylformamide) is activated for 15 min and coupled to the support (Aminomethylated polystyrene or TentaGel-NH$_2$ by incubating for 4h at RT (room temperature). After washing with DMF, MeOH and THF (tetrahydrofuran) the linker derivatised support is dried under vacuum (the extent of the reaction is monitored by Kaiser's reaction.).

Example 3

Activation of the Immobilised Linker

The linker modified support as obtained in Example 2 is treated with 20% acetylchloride in methylenechloride for 16h at RT. The activated support is then rinsed with methylenechloride and dried under vacuum.

Example 4 N-terminal coupling of phenylalanine allylester

A solution of phenylalanine allylester (0.2M) and NMM (0.4M) in methylenechloride is added to the activated solid phase as obtained in Example 3 (about 20 equivalents of amino acid to immobilised linker) and the coupling reaction allowed to proceed for 16h at RT. The solid phase is then washed with DMF, MeOH and THF. Similarly other amino acid residues are coupled to the solid phase using appropriate amino acid allylesters.

Example 5

Further Coupling of a Phenylalanine Methylester to the Solid Phase

The immobilised phenylalanine allylester as prepared in Example 4 is deprotected by treatment with a solution of (PdPPh$_3$)$_4$ (Tetrakis(triphenylphosphine)-palladium, 12.5 mmol) and morpholine (125 mmol) in methylenechloride for 1 h at RT. The phenylalanine product is washed thoroughly, activated by treatment with TBTU (0.1 M) and NMM (0.2M) in DMF for 30 min at RT and then treated with a solution of phenylalanine methylester (0.1 M) and NMM (0.2M) in DMF for 2 h at RT to yield a product in which the dipeptide ester —Phe—Phe—OMe is coupled to the solid phase. Similarly other and further amino acids are coupled analogously to the solid phase.

Example 6

Recovery of H—Phe—PheOMe from the Solid Phase

The immobilised dipeptide ester as prepared in Example 5 is treated with an aqueous solution of trifluoroacetic acid (TFA) (95% TFA/5% H$_2$O) to quantitatively cleave the dipeptide ester from the solid phase and yield a product in substantially pure state as judged by HPLC and ESMS.

Amino acid loading may be controlled by appropriate amino acid analysis

Example 7

Comparative Example—Investigation of the Acid Stability of Various Trityl linkers As in Example 4 above phenylalanine allylester is coupled to the solid phase using various trityl linkers: 4-[bis-(phenyl)-hydroxy-methyl]-benzoic acid (Trt); 4-[bis-(4-chloro-phenyl)-hydroxy-methyl]-benzoic acid (DCT); 4-[bis-(4-fluoro-phenyl)-hydroxy-methyl]-benzoic acid (DFT), and 4-[bis-(4-methoxy-phenyl)-hydroxy-methyl]-benzoic acid (DMT). For each linker, separate samples of the immobilised phenylalanine allylester are then treated with 5 different TFA solutions: 1.1% TFA/10% MeOH/DCM, 2.3% TFA/10% MeOH/DCM, 3. 5% TFA/10% MeOH/DCM, 4.20% TFA/10% MeOH/DCM, and 95% TFA/5% H$_2$O for 30 min at RT each. The cleavage of the phenylalanine allylester from the solid phase is followed by HPLC and analysis of the elution peaks for phenylalanine allyester. The results obtained are summarized as follows:

Cleavage conditions (comparison of the 4 linkers: DCT, DFT, Trt, DMT)

| | Conditions |
|---|---|
| 1 | 1% TFA/10% MeOH/DCM |
| 2 | 3% TFA/10% MeOH/DCM |
| 3 | 5% TFA/10% MeOH/DCM |
| 4 | 20% TFA/10% MeOH/DCM |
| 5 | 95% TFA/5% H$_2$O |

| Phe-OAllyl: | |
|---|---|
| a) DCT-Linker | |
| 1 | 2% (% relativ to conditions 5) |
| 2 | 6% |
| 3 | 24% |
| 4 | 78% |
| 5 | 100% |
| b) DFT-Linker | |
| 1 | 8% (% relativ to conditions 5) |
| 2 | 41% |
| 3 | 94% |
| 4 | 91% |

-continued

| | |
|---|---|
| 5 | 100% |
| c) Trt-Linker | |
| 1 | 17% (% relativ to conditions 5) |
| 2 | 95% |
| 3 | 90% |
| 4 | 107% |
| 5 | 100% |
| d) DMT-Linker | |
| 1 | 100% (% relativ to conditions 5) |
| 2 | 112% |
| 3 | 112% |
| 4 | 115% |
| 5 | 100% |

As internal standards glycine (Gly) is coupled to unmodified solid phase using a very stable amide bond which is not cleaved by TFA treatment. The free amino terminus of the immobilised Gly is modified with the above linkers again resulting in a very stable amide bond, and the first building block (phenylalanine allylester) is coupled to the linker via the amine trityl bond. These solid phase standards are subjected to TFA treatments as above, following which the solid phase standards samples are quenched with 20% ethanolamine in DMF and washed extensively with sonication. The solid phase standards samples are then subjected to amino acid analysis using highly acidic conditions which are sufficient to cleave all the amide bonds present, including both any remaining phenylalanine allylester from the linker and Gly from the solid phase. Thus the ratio of Phe to Gly found in this amino acid analysis is indicative of the rate of cleavage during the TFA treatments. The results of the amino acid analysis for the TFA treated solid phase standards samples as described above are summarized as follows.

| | Gly | Phe-OAllyl |
|---|---|---|
| a) DCT-Linker | | |
| 1 | 103% | 100% |
| 2 | 85% | 100% |
| 3 | 70% | 100% |
| 4 | 4% | 100% |
| 5 | 2% | 100% |
| b) DFT-Linker | | |
| 1 | 50% | 100% |
| 2 | 35% | 100% |
| 3 | 5% | 100% |
| 4 | 2% | 100% |
| 5 | 5% | 100% |
| c) Trt-Linker | | |
| 1 | 65% | 100% |
| 2 | 22% | 100% |
| 3 | 5% | 100% |
| 4 | 3% | 100% |
| 5 | 3% | 100% |
| d) DMT-Linker | | |
| 1 | 4% | 100% |
| 2 | 4% | 100% |
| 3 | 2% | 100% |
| 4 | 4% | 100% |
| 5 | 4% | 100% |

These data clearly confirm the HPLC results. For all conditions used the amino acid is totally cleaved from the DMT-linker system for the TFA-treated samples. The treated Trt- and DFT-linker samples show comparable behaviour. However the results for the treated DCT-linker samples indicate good stability to TFA at concentrations up to at least about 5%.

I claim:

1. A compound of formula II

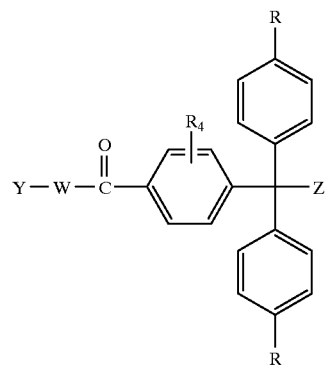

wherein $R_4$ is alkyl, halogen, $NO_2$, or hydrogen;

Z is a coupling group chosen from acylamido, acyloxy, amino, halogen, thiol or hydroxyl,
where acyl is a residue of formula $R_5CO$ where $R_5$ is an organic group;

Y is H, a reactive functional group or an attachment to a solid phase;

W is O when Y is H or a reactive functional group, or W is —NH—, or —$NR_6$— (urethane) when Y is an attachment to a solid phase,
where $R_6$ is an organic group and, each R which, may be the same or different, is $C(O)NR_7R_8$, $CF_3$, F or Cl wherein each $R_7$ and $R_8$, which may be the same or different, is H or $C_{1-4}$ lower alkyl wherein the compound of formula II is resistant to moderate or strongly acidic conditions employed during solid phase chemical synthesis.

2. A compound according to claim 1, in which $R_4$ is hydrogen.

3. A compound according to claim 1, in which Z is selected from the group consisting of OH and halogen.

4. A compound according to claim 1, in which W is —O— or —NH—.

5. A compound according to claim 1 in which R is selected from the group consisting of $C(O)NR_7R_8$, $CF_3$ and Cl.

6. A solid phase synthesis system of formula II

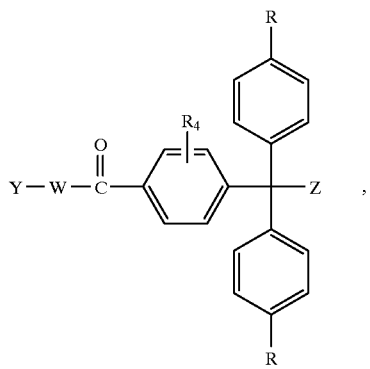

wherein $R_4$, Z, W and R are as defined in claim 1 and Y is a solid phase support material.

7. A process for the preparation of a solid support system according to claim 6 comprising coupling a compound of formula II in which $R_4$, Z, W and R are as defined in claim 1 and Y is H, or a reactive functional group with a suitably derivatised or functionalised solid phase material.

* * * * *